(12) United States Patent
Köhler

(10) Patent No.: US 10,868,964 B2
(45) Date of Patent: Dec. 15, 2020

(54) OPTICAL OBSERVATION SYSTEM AND METHOD FOR OPERATING AN OPTICAL OBSERVATION SYSTEM

(71) Applicant: KARL STORZ SE & Co. KG, Tuttlingen (DE)

(72) Inventor: Benedikt Köhler, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 0 days.

(21) Appl. No.: 16/589,282

(22) Filed: Oct. 1, 2019

(65) Prior Publication Data

US 2020/0112683 A1    Apr. 9, 2020

(30) Foreign Application Priority Data

Oct. 4, 2018   (DE) .................. 10 2018 124 496

(51) Int. Cl.
*H04N 5/232*     (2006.01)
*A61B 1/00*     (2006.01)
(Continued)

(52) U.S. Cl.
CPC ..... *H04N 5/23296* (2013.01); *A61B 1/00009* (2013.01); *H04N 5/2628* (2013.01); *H04N 2005/2255* (2013.01)

(58) Field of Classification Search
CPC .............. H04N 5/23296; H04N 5/2628; A61B 1/00009; A61B 1/00183
See application file for complete search history.

(56) References Cited

U.S. PATENT DOCUMENTS 6,491,628 B1 * 12/2002 Kobayashi ......... A61B 1/00059
                                              600/168
7,477,297 B2    1/2009 Pollard
(Continued)

FOREIGN PATENT DOCUMENTS

DE             10126587 A1   12/2001
DE     102015121017 A1    6/2017
(Continued)

OTHER PUBLICATIONS

German Search Report for corresponding German Patent Application No. 10 2018 124 496.7, dated Jun. 28, 2019.

*Primary Examiner* — Ahmed A Berhan
(74) *Attorney, Agent, or Firm* — Jason H. Vick; Sheridan Ross, PC

(57) ABSTRACT

An optical observation system (1) according to the invention comprises an optical observation apparatus, more particularly an endoscope or an exoscope (2), comprising an imaging optical unit and an electronic image recorder, wherein the imaging optical unit is embodied to image an object field (3) on the electronic image recorder with an alterable imaging scale and the electronic image recorder is embodied to produce recorded image data of the object field (3), an image display apparatus for presenting at least a section of the object field (3) and an image processing apparatus (20), which is configured to produce display image data by scaling the recorded image data with an alterable scaling factor and to actuate the image display apparatus with the display image data. According to the invention, the imaging scale is alterable over a plurality of levels and the scaling factor is continuously alterable, wherein the scaling factor is coupled to the optical imaging scale in such a way that the scaling factor is changed in the opposite sense when the optical imaging scale is altered. The (Continued)

invention also relates to a method for operating an optical observation system (1).

15 Claims, 4 Drawing Sheets

(51) Int. Cl.
*H04N 5/225* (2006.01)
*H04N 5/262* (2006.01)

(56) References Cited

U.S. PATENT DOCUMENTS

| | | |
|---|---|---|
| 7,794,396 B2 | 9/2010 | Gattani et al. |
| 2002/0154912 A1* | 10/2002 | Koseki ............... H04N 5/23293 396/429 |
| 2003/0179303 A1* | 9/2003 | Bittner ................. H04N 5/2254 348/240.3 |
| 2009/0062604 A1* | 3/2009 | Minosawa ......... A61B 17/3423 600/104 |
| 2013/0229502 A1 | 9/2013 | Kutsuma et al. |
| 2015/0085084 A1 | 3/2015 | Heni et al. |
| 2016/0286197 A1 | 9/2016 | Schwarz et al. |
| 2017/0163972 A1 | 6/2017 | Köhler et al. |

FOREIGN PATENT DOCUMENTS

| | | |
|---|---|---|
| EP | 2850996 A1 | 3/2015 |
| EP | 2656776 B1 | 3/2016 |
| EP | 3073307 A1 | 9/2016 |

\* cited by examiner

OPTICAL OBSERVATION SYSTEM AND METHOD FOR OPERATING AN OPTICAL OBSERVATION SYSTEM

CROSS REFERENCE TO RELATED APPLICATIONS

This application claims the benefit under 35 U.S.C. 119(a) to German Patent Application No. 10 2018 124 496.7, filed Oct. 4, 2018, the disclosure of which is incorporated herein by reference in its entirety.

The present invention relates to an optical observation system according to the preamble of claim 1, comprising an optical observation apparatus, more particularly an endoscope or an exoscope, an image display apparatus and an image processing apparatus. Furthermore, the present invention relates to a method for operating an optical observation system.

These days, endoscopes are used for a multiplicity of applications in medicine and technology. Typically, an endoscope comprises a rigid or flexible elongate shaft that is suitable for insertion into a cavity and that has, disposed in the distal end region thereof, i.e., the end region distant from the observer, an objective lens for producing an image of an object field situated in the cavity. An electronic image recorder, for example a CCD image sensor, can be provided in the region of the distal end of the shaft and electrical lines can be provided within the shaft, for the purposes of recording and transmitting the endoscopic image from the distal end of the endoscope to the proximal end, i.e., the end close to the observer. Alternatively, an image transmitter can be disposed in the shaft, said image transmitter comprising a plurality of relay lens systems or a coherent bundle of optical fibers and transmitting the image produced by the objective lens to the proximal end region of the endoscope, where an electronic image recorder may be disposed and/or a video camera with an electronic image recorder is connectable.

Further, an apparatus is known for observing and illuminating an object field on a patient from a location away from the body of the patient, said apparatus comprising, at the distal end of a shaft, a head part with an illumination unit for illumination purposes and an objective lens for producing an image of the object field. The image constructed by the objective lens can be recorded by an electronic image recorder disposed in the head part or else, for example, can be forwarded to an image recorder disposed at the proximal end of the shaft. Such an apparatus, which has a similar structure to an endoscope in many aspects and which facilitates the observation of an operating field in the case of a surgical operation from a working distance in the range of, typically, approximately 20 to 75 cm, is referred to as an "exoscope" and is described, e.g., in EP 2 850 996 A1 and in EP 3 073 307 A1, said documents being incorporated in this respect in the present application by reference. Exoscopes of the aforementioned type are commercially available from KARL STORZ SE & Co. KG under the trade name VITOM®.

The image recorded by the distally or proximally disposed electronic image recorder can be evaluated by an image processing apparatus that is connectable to the proximal end of the endoscope or of the exoscope, can be presented for an user and/or further persons on an image display apparatus such as, for instance, a monitor, and/or can be stored, for example for documentation purposes. Displaying a magnified image of at least one region of interest of the object field, observed by the endoscope or exoscope, on the monitor is often desirable in order to allow the user to identify additional details in the region of interest. Here, the ability to alter a magnification factor of the displayed image without steps, i.e., continuously, is particularly desirable.

U.S. Pat. No. 7,477,297 B2 has disclosed a zoom apparatus for digital image processing, said zoom apparatus comprising an optical zoom lens system with a continuous zoom range, an image sensor for recording the image produced by the optical zoom lens system and a digital zoom device for applying one of at least two discrete magnification levels on the digital representation of the recorded image. The overall magnification is the product of the discrete digital zoom level and the magnification of the optical zoom, with a digital interpolation being effected in a transition time between two discrete zoom levels.

According to U.S. Pat. No. 7,794,396 B2, video frames produced by a surgical camera are analyzed by means of image analysis algorithms for the presence of defined patterns, colors, movements, etc., which represent a defined surgical instrument or anatomical feature. Once a surgical instrument or anatomical feature has been detected, the system can automatically adapt the actual or effective focal length range of the surgical camera and thus alter the magnification or the zoom level of the camera.

EP 2 656 776 B1 has disclosed an endoscope system that comprises a zoom lens in an optical system, a photoelectric conversion element and an electronic zoom means, wherein edge components are detected in the image recorded by the photoelectric conversion element and a contour amplification signal is produced thereby, and wherein an electronic zoom region is determined in the recorded image on the basis of the strength of the contour amplification signal. Here, a number of electronic zoom scaling factors are predetermined.

On account of their structure, optical zoom lens systems are very complicated and expensive. Further, an increasing magnification in an optical zoom is linked, as a matter of principle, to a reduction in the image brightness; an increase in the image brightness requires correspondingly larger lenses, which, particularly in the case of endoscopes and exoscopes, would lead to an unwanted increase in the dimensions and in the weight of the optical system. On the other hand, a digital zoom is often linked to a deterioration in the image quality.

It is an object of the present invention to specify an optical observation system and a method for operating an optical observation system, wherein the aforementioned disadvantages are avoided to the greatest possible extent, in particular wherein a continuous zoom effect is obtainable within a given zoom range by means of a less complicated optical system.

This object is achieved by an apparatus as claimed in claim 1 and by a method as claimed in claim 13.

Advantageous developments of the invention arise from the dependent claims.

An optical observation system according to the invention comprises an optical observation apparatus comprising an imaging optical unit and an electronic image recorder. The imaging optical unit is embodied to image an object field on the electronic image recorder with an alterable imaging scale. In particular, the object field is an object field on or in a human or animal body. By way of example, the optical observation apparatus can be embodied as an exoscope or as an endoscope. In particular, the optical observation apparatus is a medical observation apparatus, for example a medical exoscope or a medical endoscope. However, the optical observation apparatus can also be destined for non-medical applications and, for instance, can be embodied to observe a technical article, wherein the object field can be an object field in or on the technical article. Here, "optical" is understood to mean, in particular, the spectral range of visible light, wherein, however, the infrared and/or the ultraviolet spectral range may also be included.

The imaging optical unit is embodied and disposed in such a way that the object field is imaged on an active surface of the electronic image recorder with an alterable imaging scale. The imaging scale, which is also referred to as "optical imaging scale" here, may be greater than 1, corresponding to a magnified image, less than 1, corresponding to a reduction in size, or else equal to 1, corresponding to an image of the object field with unchanged size.

The electronic image recorder is embodied to produce recorded image data of the imaged object field. By way of example, the electronic image recorder can be a CCD image sensor. The recorded image data represent the image of the object field produced on the active surface of the electronic image recorder by the imaging optical unit and said image can be imaged in a magnified or reduced fashion, or else with the same scale, in accordance with the optical imaging scale. The active surface of the electronic image recorder has a number $n_1$ of pixels. The recorded image data consequently represent the image data of the $n_1$ pixels.

Furthermore, the optical observation system comprises an image display apparatus for presenting at least a section of the object field to a user and, optionally, to further persons. By way of example, the image display apparatus can be a screen (monitor), projector (beamer) or else, for instance, video glasses (head-mounted display). Preferably, the image display apparatus allows a display of a currently recorded image, on the basis of which the user can operate the optical observation apparatus and, for example, can move to a desired object field or to a region of interest in the object field.

Further, the optical observation system comprises an image processing apparatus, embodied to produce display image data from the recorded image data and to actuate the image display apparatus so as to present at least a section of the object field. To this end, the image processing apparatus is connected to the electronic image recorder and the image display apparatus. The image processing apparatus is configured to scale the recorded image data with an alterable scaling factor. Methods for scaling image data in digital image processing are known per se, for example by means of interpolation, pixel repetition or other reconstruction filters. The scaling carried out by the image processing apparatus is also referred to as "electronic scaling" or "digital zoom" here. The alterable scaling factor, which is also referred to as "electronic scaling factor", can be greater than 1, less than 1 or else equal to 1. By scaling with a scaling factor of greater than 1, the recorded image data, which correspond to the recorded image data of a number $n_2$ of pixels of the electronic image recorder, are converted to be displayed on a number $n_3$ of pixels of the image display apparatus and provided as display image data for the display on the image display apparatus. Here, $n_2$ denotes the number of pixels of the image recorder on which the image of the object field constructed by the imaging optical unit, or a section of same to be displayed on the image display apparatus, is imaged; i.e., $n_2 \leq n_1$. The pixel number $n_3$ denotes, in particular, a total pixel number of the image display apparatus or the number of pixels that are used for the display of the object field or the section to be displayed.

The image processing apparatus can be embodied to carry out further steps, for instance storing image data, controlling the optical observation apparatus and/or the image display apparatus, and/or selecting the section of the image recorded by the electronic image recorder to be displayed. To this end, the optical observation apparatus, the image processing apparatus and/or the image display apparatus may comprise appropriate operating elements for actuation by the user or may be connected to a corresponding operating apparatus. By way of example, scaling can be carried out as described in DE 10 2015 121 017 A1 and can be controlled by an operating apparatus, said document being incorporated in this respect by reference.

If the scaling factor is less than 1, then $n_3 < n_2$; i.e., the image data of the $n_2$ pixels of the image recorder, corresponding to the section to be displayed, are provided for display on a smaller number $n_3$ of pixels of the image display apparatus. As a rule, image information is lost in the process; however, there is typically no visible loss in the quality of the displayed image, in particular no loss of sharpness, when compared to the case where the display is effected on the same number of pixels as the recording ($n_3 = n_2$). If the scaling factor is greater than 1, i.e., $n_3 > n_2$, the image data of the section are provided for display on a number $n_3$ of pixels of the image display apparatus that is greater than the number of pixels $n_2$ of the electronic image recorder, on which the section of the object field to be displayed is imaged, or even greater than the number $n_1$ of the pixels of the active surface of the electronic image recorder. In this case, the displayed image may lose sharpness, for example as a result of interpolation between adjacent pixels; however, this is dependent on the scaling method employed.

Consequently, the image of the object field presented on the image display apparatus has an imaging scale that depends on the optical imaging scale and the scaling factor. Below, the product of the optical imaging scale and the electronic scaling factor is referred to as "overall zoom factor". An overall magnification of the presented image is given by the overall zoom factor and, optionally, by further factors which may be determined by the pixel dimensions of the electronic image recorder and of the image display apparatus, in particular. Here, the term "magnification" may also comprise a reduction in size, with the magnification factor being less than 1 in this case. Particularly in the case of surgical applications, being able to achieve a magnification factor that is greater than 1, i.e., where the presentation of the displayed section on the image display apparatus is larger than the real size of the relevant section of the object field, is often desirable.

According to the invention, the optical imaging scale is alterable in step-wise fashion or in discrete steps, wherein at least two different imaging scales are provided. Consequently, the imaging optical unit is embodied so as to facilitate the production of an image of the object field on the electronic image recorder with a plurality of different imaging scales, specifically at least two different imaging scales, wherein the different imaging scales differ by a level magnitude that differs from zero and, in particular, is at least approximately 10%, preferably at least approximately 50%, for example approximately 100% of the respective lower imaging scale at the respective level.

Furthermore, according to the invention, the electronic scaling factor is continuously alterable. The expression "continuously" may also comprise a quasi-continuous change that is implemented in discrete steps, but the steps are so small that they cannot be perceived by a user. Thus, for example, a change of the scaling factor in discrete steps that correspond to a change in the size of the image section displayed on the image display apparatus of less than one pixel is likewise referred to as "continuous" here. Such continuous or quasi-continuous scaling is also known per se.

According to the invention, the scaling factor is further coupled to the optical imaging scale in such a way that the scaling factor is changed in the opposite sense when the optical imaging scale is altered. In particular the image processing apparatus is configured in such a way that there automatically is a respective opposing change of the optical imaging scale and the scaling factor. Provision can also be made of a control device that is configured for appropriate control of the optical observation apparatus and the image processing apparatus.

What can be achieved as a result of the scaling factor of the electronic scaling being changed in the opposite sense to the optical imaging scale when the optical imaging scale is altered is that, in the case of a step-wise change in the imaging scale, the overall magnification of the image presented on the image display apparatus does not alter or, in any case, alters to a smaller extent than would correspond to the change of the imaging scale. Consequently, this facilitates having no change, or only a small change, in the magnification or reduction of the presentation of the object field on the image display apparatus despite the step-wise change in the optical imaging scale, as a result of which a user or any other observer of the displayed image can orient themselves more easily within the image. Consequently, a magnification that is alterable in smaller steps can be achieved using a simple, cost-effective and space-saving imaging optical unit. This can facilitate an improved identification of details in the object field, wherein the fact that the image brightness does not change as a result of the electronic scaling can additionally be exploited; this facilitates an improvement in the signal-to-noise ratio, particularly in the case of applications with a low image brightness, for instance in fluorescence imaging. Since a change of the optical imaging scale and an electronic scaling or digital zoom are combined here, such a zoom may also be referred to as a "hybrid zoom".

Preferably, the image processing apparatus is configured in such a way that the electronic scaling factor is automatically changed in such a way when the optical imaging scale is altered that the product of the optical imaging scale and the electronic scaling factor is at least approximately unchanged when changing the optical imaging scale. In particular, the electronic scaling factor is altered exactly by the inverse ratio to the optical imaging scale or altered in a manner corresponding to the inverse ratio to such an extent that a change in the overall zoom factor is not perceivable in the process. Consequently, the overall magnification remains constant for the time being when the optical imaging scale is altered in step-wise fashion. What this can achieve is that the presentation of the object field on the image display apparatus is substantially unchanged despite a change in the optical imaging scale. Here, there can be a further change in the electronic scaling factor before and/or after the change in the optical imaging scale, for instance within the scope of continuous zooming in or out. Consequently, the optical magnification can be changed when continuously altering the scaling factor during a zoom process without the zoom process becoming identifiably discontinuous. Here, an interruption in the zoom process, during which the overall magnification preferably remains constant, can be accepted for a time interval necessary, for instance for pivoting optical elements in or out; by way of example, the displayed image can be repeated during this time interval.

In particular, the image processing apparatus can be configured in such a way that the electronic scaling factor is initially continuously increased when zooming into a section of the object field, i.e., during a continuously increasing overall magnification, the optical imaging scale is increased and, at least approximately simultaneously, the electronic scaling factor is reduced in such a way that the overall magnification remains unchanged in at least one transition region and, thereupon, the electronic scaling factor is continuously increased again. Further, the image processing apparatus can be configured in such a way that the electronic scaling factor is initially continuously reduced when zooming out of a section of the object field, i.e., during a continuously decreasing overall magnification, the optical imaging scale is reduced and, at least approximately simultaneously, the electronic scaling factor is increased in such a way that the overall magnification remains unchanged in the at least one transition region and, thereupon, the electronic scaling factor is reduced continuously again. As a result of this, a continuous zoom effect can be achieved when zooming in and out, despite the merely step-like, discontinuous change in the optical imaging scale, for which an imaging optical unit with a simple structure is sufficient.

For the purposes of altering the optical imaging scale, provision can advantageously be made for one or more optical elements to be introducible into a beam path of the imaging optical unit or to be removable from the beam path, for example by pivoting in or out or by pushing in or out. By way of example, pivoting in and out can be implemented using a mechanism as disclosed in EP 3 073 307 A1 for pivoting a filter in and out; in this respect, the cited document is incorporated into the present application by reference. As an alternative or in addition, one or more optical elements may be axially displaceable in the beam path of the imaging optical unit for the purposes of altering the optical imaging scale, for example in a manner known per se like in a zoom optical unit, the latter however only needing to be designed for a plurality of discrete different magnifications. Further alternatively or additionally, altering the optical imaging scale can be achieved by one or more deformable optical elements in the beam path of the imaging optical unit, wherein provision can be made of a liquid lens, for example. This facilitates the realization of at least two different optical imaging scales in a simple manner and with a compact structure. Preferably, the different optical imaging scales differ by at least approximately 10%, particularly preferably by at least approximately 50%, for example by approximately 100%.

Preferably, the imaging optical unit is embodied for a selective realization of more than two different optical imaging scales, for example, for three, four or more discrete different optical imaging scales. Here, the optical imaging scales at each level can differ, for example, by at least approximately 10%, preferably by at least approximately 50%, for example by approximately 100%. Particularly preferably, the ratio of the imaging scales is approximately 1.5 or approximately 2 if the imaging scale is altered in step-wise fashion. This allows the realization of a particularly large overall magnification range using a simple imaging optical unit.

According to a preferred embodiment of the invention, the number of pixels $n_1$ of the electronic image recorder is greater than the number of pixels $n_3$ of the image display apparatus, for which the display image data are provided by the image processing apparatus. In the case where the pixels are respectively arranged in a rectangular grid with preferably approximately the same side ratio, a number of pixels $n_1'$ along one longitudinal side of the grid in which the pixels of the electronic image recorder are disposed is greater, in particular, than a number of pixels $n_3'$ along a corresponding longitudinal side of the grid of the pixels of the image display apparatus. Consequently, the display image data comprise fewer pixels than the recorded image data if approximately the entire image of the object field, which is imaged on the active surface of the image recorder, is presented on the image display apparatus. This means that a scaling with a scaling factor of less than 1 is implemented in this case. If a section of the object field, in which a longitudinal side corresponds to a number of pixels $n_3'$, for example, should now be presented in magnified fashion in the image display apparatus, the scaling factor can be increased to the value of 1 without a deterioration in the image quality of the displayed image setting in, in particular without there being a loss of resolution or without the displayed image being less sharp than the image imaged on the image recorder. If the following refers to "without loss", this means a display without loss of image quality, in particular without the resolution of the displayed image being less than that corresponding to the number of pixels $n_3$ or $n_3'$ of the image display apparatus. As a result of the number of pixels $n_1$ of the electronic image recorder being greater than the number of pixels $n_3$ of the image display apparatus, a digital zoom without loss in this sense can be realized in a simple manner, said digital zoom complementing the change in the optical imaging scale. As a result of this, it is possible to facilitate a magnification range with a continuous or quasi-continuous zoom that has been extended in relation to the change of the optical magnification, without loss of resolution occurring. Further, a great depth-of-field can be achievable in a simple manner as a result thereof.

Preferably, the electronic scaling factor is continuously alterable in a range from 1 to at least 1.5, preferably from 1 to at least 2. This creates a digital zoom range that is sufficient for many purposes. Moreover, a particularly large continuous overall zoom range can be achieved in conjunction with a simple imaging optical unit, which facilitates a step-wise change in the optical imaging scale by a factor of 1.5 or 2. This allows a particularly large overall zoom range, or particularly large continuous overall magnification range to be achieved using a simple imaging optical unit.

According to a particularly preferred embodiment of the invention, the relative change in the optical imaging scale at at least one level of the change of the optical imaging scale is less than the square root of the ratio $(n_1/n_3)$ of the numbers of pixels $n_1$ of the electronic image recorder and the number of pixels $n_3$ of the image display apparatus or of the ratio of the numbers of pixels of the recorded image data and of the display image data, where $n_1 > n_3$. Particularly if the pixels in each case form a rectangular grid with, preferably, approximately the same side ratio, the ratio of the greater to the smaller imaging scale during the step-wise change of the optical imaging scale is less than the ratio of the numbers of pixels $n_1'$ and $n_3'$ along corresponding longitudinal sides of the image recorder and the image display apparatus, respectively. This facilitates an overlap in a range of the change in the optical imaging scale such that the change in the optical imaging scale can be implemented when zooming in or out at different scalings, which are each without loss in the aforementioned sense; this may facilitate hysteresis.

Particularly advantageously, the image processing apparatus can be configured to zoom into a section of the object field and to zoom out of the section of the object field in such a way that when zooming in, i.e., in the case of a continuously increasing overall magnification, the electronic scaling factor is initially continuously increased, the optical imaging scale is increased in a first transition region and, at least approximately simultaneously, the electronic scaling factor is reduced in such a way that the overall magnification remains unchanged and, thereupon, the electronic scaling factor is continuously increased again; and that when zooming out, i.e., in the case of a continuously decreasing overall magnification, the electronic scaling factor is initially continuously reduced, the optical imaging scale is reduced in a second transition region and, at least approximately simultaneously, the electronic scaling factor is increased in such a way that the overall magnification remains unchanged, and, thereupon, the electronic scaling factor is continuously reduced again. As a result of this, a continuous zoom effect can be achieved when zooming in and out despite the merely step-shaped, discontinuous change in the optical imaging scale, for which an imaging optical unit with a simple structure suffices.

Here, the second transition region lying at a greater overall magnification than the first, or vice versa, is further particularly advantageous. Consequently, the optical imaging factor is changed at a higher overall zoom factor when zooming out than when zooming in, or vice versa, corresponding to a change at a different time (i.e., an earlier or later time) when zooming out than the change when zooming in. This can avoid a bothersome change in the optical imaging scale and a corresponding interruption of the course of time, for instance as a result of pivoting in or out optical elements if work is only carried out in a small overall zoom range. This likewise avoids a state of the system in which a constant change, i.e., constant pivoting in and out, of the optical element is triggered when zooming around a certain magnification. In the case of a corresponding ratio of the numbers of pixels $n_1$ or $n_1'$ of the image recorder and $n_3$ or $n_3'$ of the image display apparatus, this can facilitate a loss-free continuous zoom with hysteresis.

Furthermore, a section of the image imaged on the image recorder is preferably selectable in the recorded image data, the display image data being produced on the basis of said section and said section being able to be presented in magnified fashion on the image display apparatus. This can improve the identification of details that are situated in a section of the object field selectable by the user.

According to a preferred embodiment of the invention, the imaging optical unit has a multi-channel embodiment. Thus, the optical observation apparatus can be embodied, for example, in the style of a stereo optical unit, for instance a stereo exoscope or a stereo endoscope. In particular, provision can be made of two parallel imaging optical units that each construct an image of the object field on an associated electronic image recorder, the image processing apparatus being configured to produce a stereo image from the two images with different viewing directions and to actuate a corresponding image display apparatus, for instance a stereo display or video glasses.

The present invention also relates to a method for operating an optical observation system. The optical observation system comprises an optical observation apparatus comprising an imaging optical unit and an electronic image recorder, wherein the imaging optical unit is embodied to image an object field on the electronic image recorder with an optical imaging scale that is alterable over a plurality of levels. Furthermore, the optical observation system comprises an image display apparatus for presenting at least a section of the object field with an overall magnification. In particular, the optical observation system is embodied as described above.

According to the method according to the invention, an image of an object field is recorded on the electronic image recorder with a first optical imaging scale and said image is displayed on the image display apparatus with a continuously alterable electronic scaling in a first overall magnification range. The optical imaging scale is altered in relation to the first imaging scale by an absolute value that differs from zero and, at least approximately simultaneously, the electronic scaling is altered in the opposite sense in a transition region to a second overall magnification range adjacent to the first overall magnification range. The image of the object field is likewise presented on the image display apparatus with a continuously alterable electronic scaling in the second overall magnification range.

When the optical imaging scale is altered, the electronic scaling factor is preferably changed in such a way that the product of the optical imaging scale and the scaling factor remains substantially constant; what this can achieve is that the image displayed on the display apparatus has an unchanging overall magnification during the change in the optical imaging scale. In particular, the electronic scaling factor can initially be continuously increased when zooming into a section of the object field, the optical imaging scale can be increased in a first transition region and, at least approximately simultaneously, the electronic scaling factor can be decreased in such a way that the overall magnification remains unchanged in the process, and, thereupon, the electronic scaling factor can be increased continuously again. Furthermore, provision can be made for the electronic scaling factor to be initially continuously reduced when zooming out of the section of the object field, the optical imaging scale being reduced in a second transition region and, at least approximately simultaneously, the electronic scaling factor being increased in such a way that the overall magnification remains unchanged, and, thereupon, the electronic scaling factor being continuously reduced again. Here, the first and the second transition region can lie at different overall magnifications; in particular, should the number of pixels of the electronic image recorder be correspondingly larger than that of the display apparatus, the first transition region can lie at a higher overall magnification than the second transition region.

Further advantageous configurations of the method according to the invention emerge from the above description of the optical observation system.

It is understood that the features specified above and the features yet to be explained below are usable not only in the combination specified in each case, but also in other combinations or on their own without departing from the scope of the present invention.

Further aspects of the invention emerge from the following description of preferred exemplary embodiments and the attached drawing. In detail:

Figure 3:
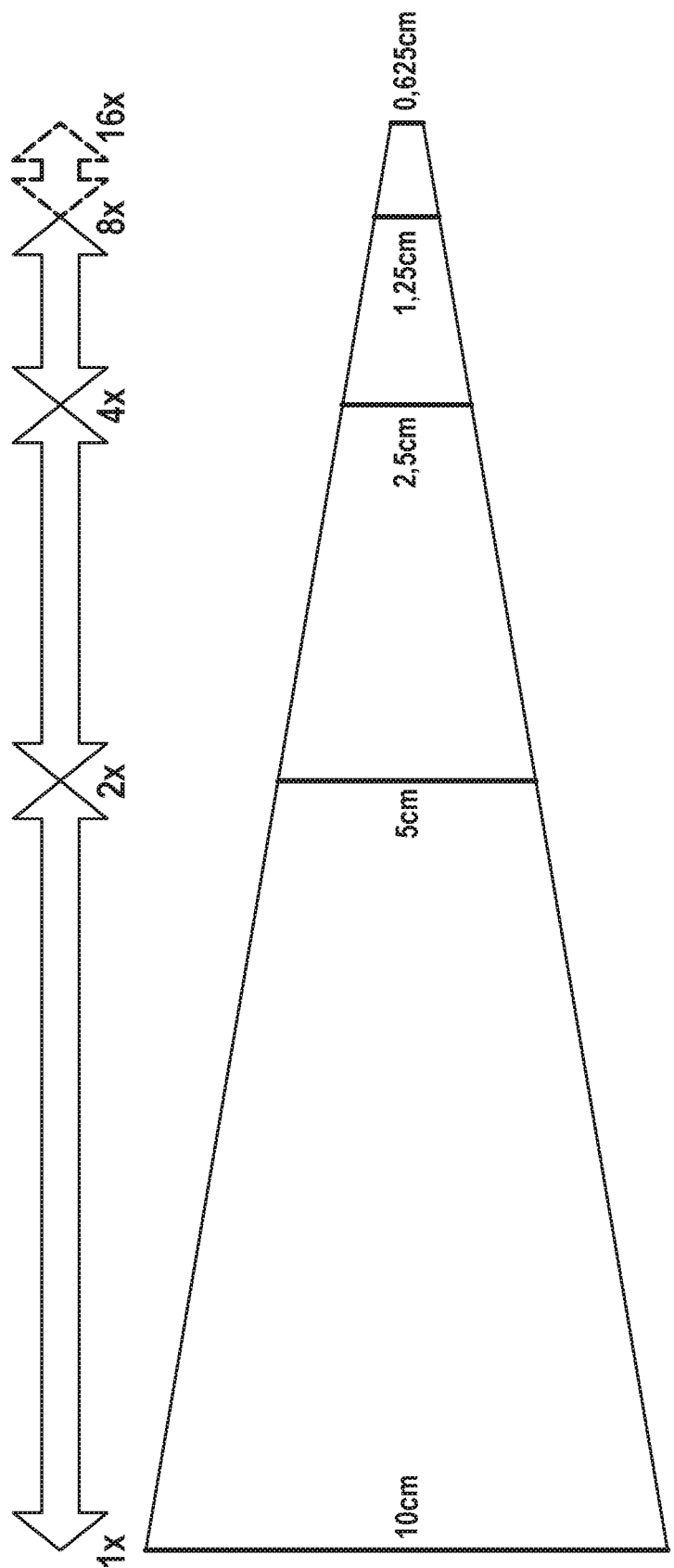
Figure 4:
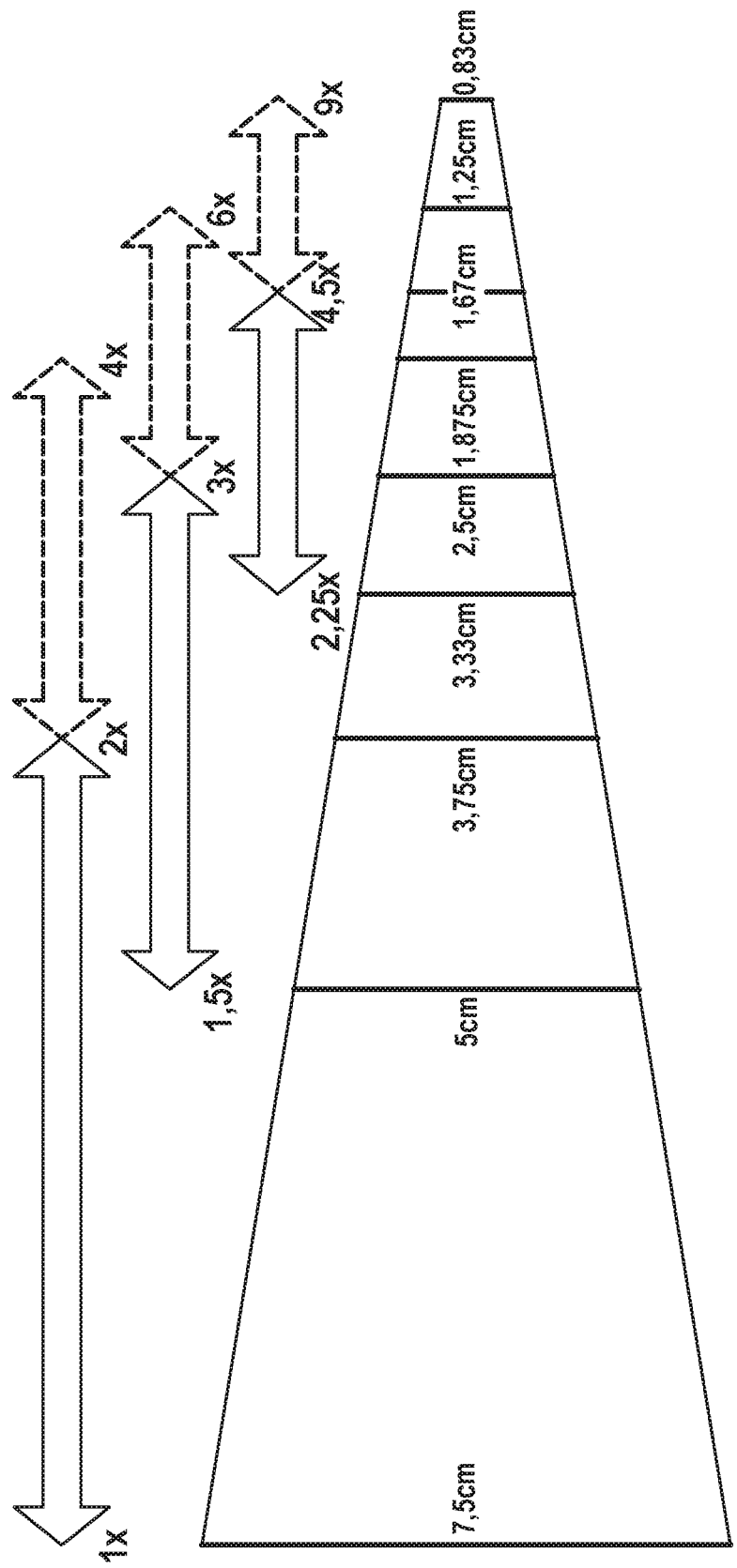

FIG. 3 schematically shows a zoom process according to a first variant of the method according to the invention;

FIG. 4 schematically shows a zoom process according to a second variant of the method according to the invention.

Figure 1:
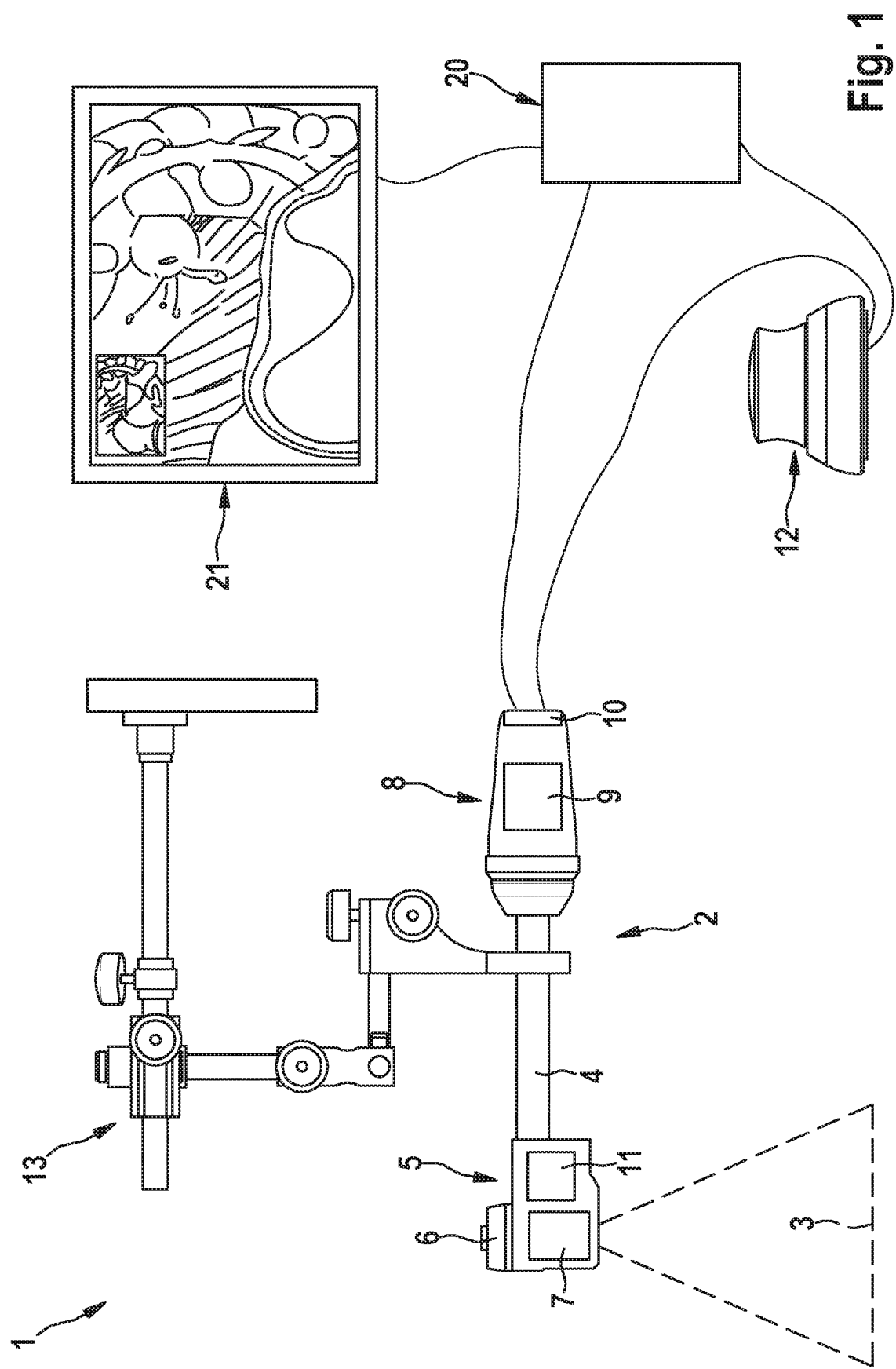
FIG. 1 shows an overview of an exemplary embodiment of an optical observation system according to the invention.

As shown in exemplary fashion in FIG. 1, an optical observation system 1 according to the invention comprises an optical observation apparatus, embodied as an exoscope 2 in the illustrated example. The exoscope 2 serves to observe an object field 3 on a human or animal body from a working distance of, for example, approximately 30 cm. The exoscope 2 comprises an approximately cylindrical shaft 4, a head part 5 being disposed on the distal end thereof. An optical unit 7 that is disposed so as to be rotatable about an axis perpendicular to the longitudinal axis of the shaft 4 by means of a rotary cap 6 is received within the head part 5. In the presented example, the optical unit 7 is embodied as a stereo optical unit and comprises two stereo channels, each with an objective lens that produces an image of the object field 3 on a respectively assigned electronic image recorder, for example a CCD image sensor. The objective lenses of the two observation channels are arranged virtually parallel to one another, wherein the optical axes of the objective lenses may be aligned to one another at an angle that corresponds to an envisaged working distance from the object field 3.

Further, the exoscope 2 comprises a handle 8, which carries display and operating elements 9 and connectors 10 for electrical signal and supply lines and which is disposed at the proximal end of the shaft 4 lying opposite the head part 5. An illumination unit 11 can be provided in the head part 5 for producing illumination light which is emitted in the direction of the object field 3; however, a connector for an optical fiber cable that can supply illumination light produced by an external light source (not illustrated in FIG. 1) may also be provided on the handle 8 for example. Furthermore, an external operating apparatus 12 may be connected, the latter serving to control the exoscope 2 and the image processing apparatus 20 described below. By way of example, the operating apparatus 12 can be configured as described in DE 10 2015 121 017 A1 and can serve, for instance, to control the overall zoom factor and the selection of a section of the object field 3 to be represented in magnified fashion.

To keep the exoscope 2 at a suitable position for observing the object field 3, provision is made of an adjustable stand 13 which, for example, can be fastened to a support or an operating table.

The optical observation system 1 furthermore comprises an image processing apparatus 20, configured to process the image signals produced by the image recorders of the optical unit 7. The processed image signals are provided for display on a monitor 21. In the illustrated exemplary embodiment, the monitor 21 is designed for stereo observation. The image processing apparatus 20 can also be configured to store the image data.

Figure 2:
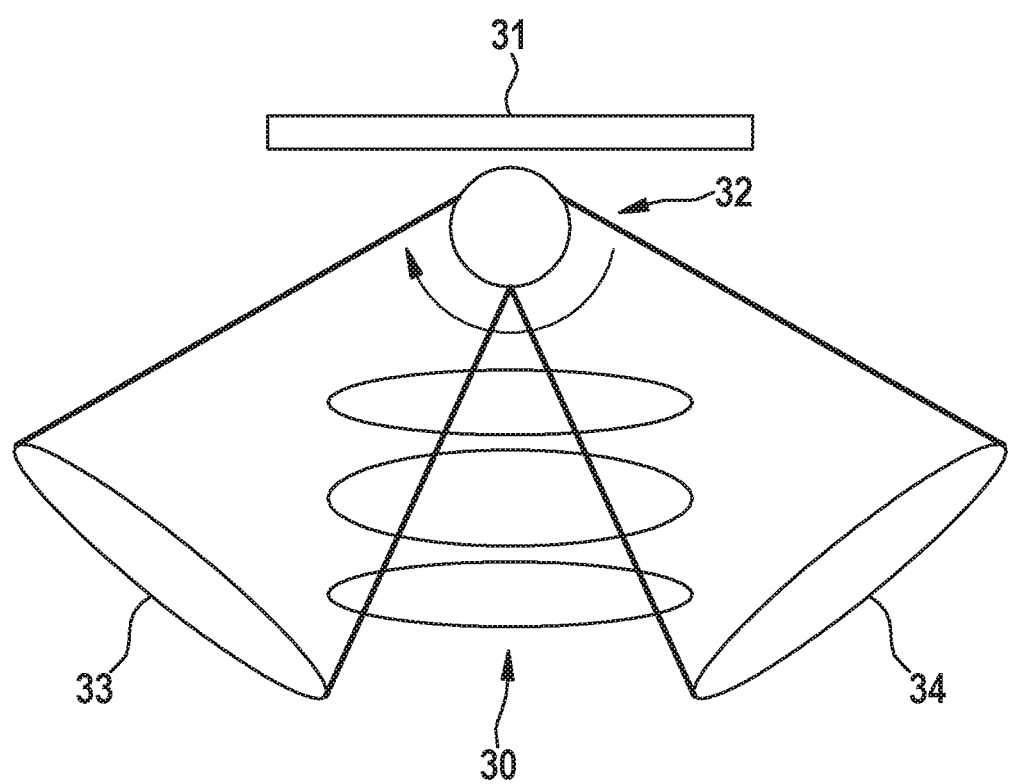
FIG. 2 shows a channel of the optical unit of the exoscope of FIG. 1 in a symbolic representation.

FIG. 2 schematically illustrates the structure of one of the two stereo channels of the optical unit 7. An image of the object field 3 is produced on the active surface of the image sensor 31 by the objective lens 30, only one lens group of which is shown, symbolically, in FIG. 2. Said image has an optical imaging scale determined by the properties of the objective lens 30 and the working distance, referred to here as "normal magnification". A pivoting mechanism 32 allows the selective pivoting of a first additional optical unit 33 or a second additional optical unit 34 into the beam path of the objective lens 30, said additional optical units each being represented symbolically as a lens. The first and second additional optical units 34 are constructed in such a way that the object field 3, or a section of same, is likewise imaged on the image sensor 31 in each case; however, this imaging is performed at a first or second optical imaging scale that differs from the normal magnification. Preferably, there is no need to change the working distance between the head part 5 of the exoscope 2 and the object field 3 when changing the imaging scale (see FIG. 1). In principle, the pivoting mechanism 32 can have a similar structure to the pivoting mechanism disclosed in EP 3 073 307 A1 for pivoting filters in and out. This facilitates a step-wise change in the optical imaging scale, specifically a change between the normal magnification and two further imaging scales; here, for example, the first imaging scale can be a reduced imaging scale in relation to the normal magnification and the second imaging scale can be an increased imaging scale in relation to the normal magnification.

FIG. 3 schematically illustrates a zoom process using the optical observation system 1, wherein the exemplary assumption is made that the first additional optical unit 33 produces a reduction with an imaging scale of 50% of the normal magnification, i.e., in relation to the imaging scale of the objective lens 30 without an additional optical unit, and the second additional optical unit 34 produces a magnification by a factor of 2 in relation to the normal magnification (see FIG. 2). Further, the assumption is made that the image sensor 31 of the relevant optical channel has approximately four times more pixels than the number of pixels required for a display on the monitor 21 without loss of sharpness, to be precise it respectively has two times the number of pixels of the monitor 21 along a horizontal and a vertical longitudinal side of a rectangular pixel grid. For instance, the image sensor 31 can be a 4 k sensor with 4096×2160 pixels and the monitor 21 can be designed as a "full HD" display with 1920×1080 pixels, or the image sensor 31 can be an 8 k sensor and the display image data can be provided as 4 k signal. Accordingly, the image processing apparatus 20 is configured for "loss-free" scaling by a factor of 2.

If the additional optical unit 33 is pivoted into the beam path of the objective lens 30 in an initial state, a square visual field, for example with an edge length of 10 cm, can be observed at a working distance of 30 cm and can be presented on the monitor 21; the specifications of the edge length made below can apply accordingly to an edge length or to a diagonal in the case of a rectangular image field, or to a diameter in the case of a circular image field. In order to obtain a continuous zoom effect, a "loss-free" digital zoom is now initially performed up to magnification by a factor of 2 by virtue of the image processing apparatus 20 providing accordingly scaled image data for display on the monitor 21. Up to the magnification factor of 2, which corresponds to an edge length of the displayed visual field of 5 cm, a magnified image can be presented without loss of sharpness in this way under the aforementioned assumptions (indicated in FIG. 3 by a solid double-headed arrow). The section of the image magnified by the digital zoom can be selected by the user within the active surface of the image sensor.

Once the magnification factor of 2 has been reached in the electronic zoom, the first additional optical unit 33 is pivoted out of the beam path of the objective lens 30; the optical imaging scale now corresponds to the normal magnification of the objective lens 30. At the same time, or at least approximately the same time, the scaling factor of the image processing apparatus 20 is moved from 2 to 1 again. The magnification of the image shown on the monitor 21 does not change in the process, and so the edge length of the visible visual field continues to be 5 cm. Therefore, the implemented change in the optical imaging scale is not identifiable by a user observing the displayed image, or said change is exhibited at best by a short interruption in the continuous zoom process, which is necessary to carry out the pivoting process of the additional optical unit 33 and during which the previously displayed image is repeated.

During the further course of the zoom process, the electronic scaling factor is continuously increased to 2 again such that an image of the object field that has been magnified in relation to the initial state by a factor of 4 overall is finally displayed on the monitor 21. Then, the edge length or the diameter of the presented section is only still 2.5 cm.

In order to further continue the zoom process, the second additional optical unit 34 is now pivoted into the beam path of the objective lens 30 and, at the same time, the electronic scaling factor is reset to 1 again. During this change of the optical imaging scale, too, the overall magnification of the image displayed on the monitor 21 remains constant, just like the size of the illustrated section of the object field, and so this change, too, is at best identifiable by the user by a brief interruption of the zoom process, caused by the mechanical pivoting.

During further zooming, the electronic scaling factor can once again be increased continuously up to 2 without an identifiable loss of imaging sharpness occurring. As a result, this renders a magnification by the factor of 8 achievable overall, with the displayed section of the object field finally only still having an edge length of 1.25 cm. Overall, this can achieve a loss-free continuous zoom effect by a factor of 8, with only three discrete different optical imaging scales being necessary. Such a loss-free electronic zoom is symbolized in FIG. 3 by solid double-headed arrows.

As additionally indicated by a dashed double-headed arrow in FIG. 3, the electronic scaling factor can be further increased so as to obtain a further magnification if a loss of sharpness of the displayed image is accepted, in order, for example, to finally obtain a 16-fold magnification in relation to the initial state overall in the case where the scaling factor is increased to 4.

In the case of a continuous reduction of the displayed image, the procedure can be carried out in a corresponding reverse sequence, with a continuous zoom effect likewise being obtainable. The zoom procedure and the selection of the image section that is electronically increased can be controlled by the user, for example by means of the external operating apparatus 12.

FIG. 4 illustrates a further variant of the method according to the invention in exemplary fashion. Here, the assumption is made that the reduction obtained by the first additional optical unit 33 corresponds to a factor of 0.67 and the magnification obtained by the second additional optical unit 34 corresponds to a factor of 1.5, in relation to the magnification obtained by the objective lens 30 on its own, i.e., in relation to the normal magnification. Like in the example explained in relation to FIG. 3, the assumption is also made here that the number of pixels along each longitudinal side of a rectangular grid in the image sensor is twice that of the corresponding longitudinal side of the image display apparatus (monitor 21).

In the initial state, the edge length or the diameter of the visible visual field is 7.5 cm in this example. Initially, an electronic scaling is undertaken up to a magnification of 2, then the first additional optical unit 33 is pivoted out of the beam path and, at the same time, the electronic scaling is reduced to 1.33. There is no change in the overall magnification of the image displayed on the monitor 21 during this change in the optical imaging scale. Thereupon, there is, again, a continuous increase in the scaling factor up to 2 when zooming further into a section of the object field 3. The overall magnification now is 3 and the edge length of the displayed section is 2.5 cm. Now, there is a renewed change in the optical imaging scale by pivoting in the second additional optical unit 34, with the electronic scaling simultaneously being set to 1.33. Then the scaling is again continuously increased up to 2 when zooming further in. This now achieves an overall magnification of 4.5 in relation to the initial state without a loss of sharpness of the displayed image occurring, i.e., the zoom is "loss free" (indicated by solid double-headed arrows in FIG. 4). The edge length of the image section presented with the magnification of 4.5 is 1.67 cm.

As indicated further in FIG. 4, an additional magnification by further scaling with a greater factor than 2 is possible in each of the three levels of the optical imaging scale if a loss of sharpness is accepted in the process (symbolized by dashed double-headed arrows). In total, this can obtain, for example, a 9-fold overall magnification in relation to the initial state, with the displayed magnified section of the object field 3 only still having an edge length of 0.83 cm.

As further indicated in FIG. 4, the changes of the optical imaging scale when zooming out can occur at different overall magnifications, more particularly lower overall magnifications, than when zooming-in as described above. In the illustrated example, a loss-free continuous digital zoom can be carried out by reducing the electronic scaling factor from 2 to 1, for instance from the overall magnification of 4.5 to an overall magnification of 2.25, where a section with an edge length of 3.33 cm is displayed. Only then is the second additional optical unit 34 pivoted out and the scaling factor is set to 1.5 at the same time. Then, the electronic scaling is reduced continuously to 1 again during the further zooming out, with the edge length of the displayed image section then being 5 cm. Then, the first additional optical unit 33 is pivoted in and the scaling is increased to 1.5 at the same time. Finally, the scaling is continuously reduced to 1, as a result of which the initial state is reached again.

This allows a loss-free continuous zoom effect by a factor of 4.5 to be obtained, with likewise only three different optical imaging scales which each differ by factor of 1.5 being necessary, and a hysteresis is facilitated in different zoom directions. In this variant, too, the zoom process and the selection of the image section displayed in magnified fashion can be controlled, as mentioned above, by the user by way of the external operating apparatus 12.

To provide a better overview, not all reference signs are presented in all figures. Reference signs not explained in relation to one figure have the same meaning as in the remaining figures.

LIST OF REFERENCE SIGNS

1 Optical observation system
2 Exoscope
3 Object field
4 Shaft
5 Head part
6 Rotary cap
7 Optical unit
8 Handle
9 Display and operating elements
10 Connectors
11 Illumination unit
12 Operating apparatus
13 Stand
20 Image processing apparatus
21 Monitor
30 Objective lens
31 Image sensor
32 Pivoting mechanism
33 Additional optical unit
34 Additional optical unit

The invention claimed is:

1. An optical observation system, comprising an optical observation apparatus comprising an imaging optical unit and an electronic image recorder, wherein the imaging optical unit is configured to image an object field on the electronic image recorder with an alterable imaging scale and the electronic image recorder is configured to produce recorder image data of the object field, an image display apparatus configured to present at least a section of the object field and an image processing apparatus, which is configured to produce display image data by scaling the recorder image data with an alterable scaling factor and to actuate the image display apparatus with the display image data, wherein the imaging scale is alterable over a plurality of levels and the scaling factor is continuously alterable, wherein the scaling factor is coupled to the imaging scale such that the scaling factor is changed in the opposite sense when the imaging scale is altered, wherein a ratio of the imaging scales in the case of at least one step-wise change of the imaging scale is less than a root of a ratio of a number of pixels (n1) of the electronic image recorder and a number of pixels (n3) of the image display apparatus.

2. The optical observation system as claimed in claim 1, wherein the scaling factor is changed in such a way when the imaging scale is altered that the product of the imaging scale and the scaling factor is substantially constant.

3. The optical observation system as claimed in claim 1, wherein one or more optical elements are introducible into and/or axially displaceable and/or deformable within a beam path of the imaging optical unit for the purpose of altering the imaging scale.

4. The optical observation system as claimed in claim 1, wherein the imaging optical unit is embodied for selective realization of more than two different imaging scales.

5. The optical observation system as claimed in claim 1, wherein a ratio of the imaging scales in the case of a step-wise change of the imaging scale is at least approximately 1.1.

6. The optical observation system as claimed in claim 1, wherein the number of pixels n1 of the electronic image recorder is greater than the number of pixels n3 of the image display apparatus, for which the display image data are provided by the image processing apparatus.

7. The optical observation system as claimed in claim 1, wherein the scaling factor is continuously alterable in a range from 1 to at least.

8. The optical observation system as claimed in claim 1, wherein a section of the image imaged on the image recorder is selectable in the recorded image data, the display image data being produced on the basis of said section.

9. The optical observation system as claimed in claim 1, wherein the imaging optical unit has a multi-channel embodiment.

10. The optical observation system of claim 1, wherein the optical observation apparatus is an endoscope or an exoscope.

11. The optical observation system of claim 1, wherein a ratio of the imaging scales in the case of a step-wise change of the imaging scale is at least approximately 1.5.

12. The optical observation system of claim 1, wherein a ratio of the imaging scales in the case of a step-wise change of the imaging scale is at least approximately 2.

13. An optical observation system, comprising an optical observation apparatus comprising an imaging optical unit and an electronic image recorder, wherein the imaging optical unit is configured to image an object field on the electronic image recorder with an alterable imaging scale and the electronic image recorder is configured to produce recorder image data of the object field, an image display apparatus configured to present at least a section of the object field and an image processing apparatus, which is configured to produce display image data by scaling the recorder image data with an alterable scaling factor and to actuate the image display apparatus with the display image data, wherein the imaging scale is alterable over a plurality of levels and the scaling factor is continuously alterable, wherein the scaling factor is coupled to the imaging scale such that the scaling factor is changed in the opposite sense when the imaging scale is altered, wherein the image processing apparatus is configured such that, in the case of a continuously increasing overall magnification, the scaling factor is continuously increased, the imaging scale is increased in a first transition region and, at least approximately simultaneously, the scaling factor is reduced in such a way that the overall magnification remains unchanged and, thereupon, the scaling factor is continuously increased again, and/or, in the case of a continuously decreasing overall magnification, the scaling factor is continuously reduced, the imaging scale is reduced in a second transition region and, at least approximately simultaneously, the scaling factor is increased in such a way that the overall magnification remains unchanged, and, thereupon, the scaling factor is continuously reduced again.

14. The optical observation system as claimed in claim 13, wherein the first and the second transition region lie at different overall magnifications.

15. The optical observation system as claimed in claim 13, wherein the second transition region corresponds to a greater overall magnification than the first transition region.

* * * * *